United States Patent
Kato

(10) Patent No.: US 11,420,871 B2
(45) Date of Patent: Aug. 23, 2022

(54) POLYOXOMETALATE COMPOUND AND METHOD FOR PRODUCING SAME, SINTERED BODY OF POLYOXOMETALATE COMPOUND, AND REACTION CATALYST

(71) Applicant: NATIONAL UNIVERSITY CORPORATION SHIZUOKA UNIVERSITY, Shizuoka (JP)

(72) Inventor: Chika Kato, Shizuoka (JP)

(73) Assignee: NATIONAL UNIVERSITY CORPORATION SHIZUOKA UNIVERSITY

(*) Notice: Subject to any disclaimer, the term of this patent is extended or adjusted under 35 U.S.C. 154(b) by 0 days.

(21) Appl. No.: 17/254,939

(22) PCT Filed: Jul. 3, 2019

(86) PCT No.: PCT/JP2019/026522
§ 371 (c)(1),
(2) Date: Dec. 22, 2020

(87) PCT Pub. No.: WO2020/009166
PCT Pub. Date: Jan. 9, 2020

(65) Prior Publication Data
US 2021/0122636 A1    Apr. 29, 2021

(30) Foreign Application Priority Data

Jul. 4, 2018 (JP) .............................. JP2018-127351

(51) Int. Cl.
*C01B 25/37* (2006.01)
*B01J 31/28* (2006.01)
(Continued)

(52) U.S. Cl.
CPC ............... *C01B 25/37* (2013.01); *B01J 31/28* (2013.01); *B01J 31/34* (2013.01); *B01J 35/02* (2013.01); *B01J 37/0209* (2013.01); *B01J 37/08* (2013.01)

(58) Field of Classification Search
None
See application file for complete search history.

(56) References Cited

U.S. PATENT DOCUMENTS

2012/0197033 A1    8/2012  Neumann et al. ............ 556/136

FOREIGN PATENT DOCUMENTS

| CN | 102172540 A | 9/2011 |
|---|---|---|
| JP | 2017-185469 A | 10/2017 |
| WO | WO 2007/142729 A1 | 12/2007 |

OTHER PUBLICATIONS

C.N. Kato et al., "Diplatinum(II)-coordinated polyoxotungstate: synthesis, molecular structure, and photocatalytic performance for hydrogen evolution from water under visible-light irradiation", Dalton Trans., 2012, vol. 41, pp. 10021-10027.
(Continued)

*Primary Examiner* — Yun Qian
(74) *Attorney, Agent, or Firm* — Ostrolenk Faber LLP

(57) ABSTRACT

Disclosed is a polyoxometalate compound including a metal-substituted polyoxometalate. The metal-substituted polyoxometalate includes a polyoxometalate having defect sites, a substituting metal atom introduced into the defect sites, and an organic ligand. The substituting metal atom is divalent platinum or palladium. The organic ligand may be a bidentate ligand having an aliphatic heterocycle containing two nitrogen atoms coordinately bonded to the substituting metal atom. One substituting metal atom is introduced into one defect site.

3 Claims, 10 Drawing Sheets

(51) Int. Cl.
 B01J 31/34 (2006.01)
 B01J 35/02 (2006.01)
 B01J 37/02 (2006.01)
 B01J 37/08 (2006.01)

(56) References Cited

OTHER PUBLICATIONS

C.N. Kato et al., "Syntheses and characterization of α-Keggin- and α$_2$-Dawson-type diplatinum(II)-coordinated polyoxotungstates: Effects of skeletal structure, internal element, and nitrogen-containing ligand coordinated to the platinum center for hydrogen production from water under light irradiation," Catalysis Today, 2018, vol. 332, pp. 2-10.

K. Kumamoto et al. "Visible Light-Driven Photoenergy Storage and Photocatalysis Using Polyoxometallates Coupled with a Ru Complex," The Journal of Physical Chemistry C, 2017, vol. 121, pp. 13515-13523.

Z. Lin et al., "Platinum-Containing Polyoxometalates: syn- and anti-[Pt$^{II}_2$(α-PW$_{11}$O$_{39}$)$_2$]$^{10-}$ and Formation of the Metal-Metal-Bonded di-pt$^{III}$ Derivatives," Chemistry—A European Journal, 2016, vol. 22, No. 16, pp. 5514-5519.

Partial Supplementary European Search Report dated Feb. 4, 2022 in counterpart European Application No. 19829883.8.

Chika Nozaki Kato et al.: "Hydrogen Evolution from Water under Visible-Light Irradiation Using Keggin-Type Platinum(II)-Coordinated Phospho-, Silico-, and Germanotungstates as Co-Catalysts", Modern Research in Catalsis, 2016, vol. 5, No. 4, pp. 103-129, XP055656303.

Shota Hattori et al.: "A Novel Photocatalytic System Constructed Using Eosin Y, Titanium Dioxide, and Keggin-Type Platinum(II)- and Aluminum(III)-Coordinated Polyoxotungstates for Hydrogen Production from Water Under Visible Light Irradiation", Catalysis Letters, vol. 145, No. 9, July 9, 2015, pp. 1703-1709, XP055656309.

Masao Kato et al.: "A Keggin-type polyxotungstate-coordinated diplatinum(II) complex: Synthesis, characterization, and stability of the cis-platinum(II) moieties in dimethylsulfoxide and water", Inorganic Chemistry Communications, Elsevier, Amsterdam, NL, vol. 14, No. 6, 2011, pp. 982-985, XP028204857.

Chika Nozaki Kato et al.: "Diplatinum(ii)-coordinated polyoxotungstate: synthesis, molecular structure, and photocatalytic performance for hydrogen evolution from water under visible-light irradiation", Dalton Transactions, 2012, 41, pp. 10021-10027, XP055881774.

Chika Nozaki Kato et al..: "Synthesis, Characterization, and Stability of α-Keggin-Type Polyoxotungstate-Coordinated Mono-Platinum(II) Complex", European Journal of Inorganic Chemistry, 2019, pp. 517-522, XP055882507.

POLYOXOMETALATE COMPOUND AND METHOD FOR PRODUCING SAME, SINTERED BODY OF POLYOXOMETALATE COMPOUND, AND REACTION CATALYST

CROSS-REFERENCE TO RELATED APPLICATIONS

The present application is a 35 U.S.C. §§ 371 national phase conversion of International Application No. PCT/JP2019/026522, filed Jul. 3, 2019, which claims priority to Japanese Patent Application No. 2018-127351, filed Jul. 4, 2018, the contents of both of which are incorporated herein by reference. The PCT International Application was published in the Japanese language.

TECHNICAL FIELD

The present invention relates to a polyoxometalate compound and a method for producing the same, a sintered body of a polyoxometalate compound and a reaction catalyst.

BACKGROUND ART

A polyoxometalate compound is a metal oxide containing a polyoxometalate ion composed of a plurality of base units such as a tetrahedron formed through coordinate bonding of oxygen atoms to metal atoms. In particular, when some of the base units of the polyoxometalate ion containing heteroatoms are deleted, and various substitution structures are introduced into the resulting defect site, a metal-substituted polyoxometalate compound having various functions can be obtained. For example, it has been reported that a platinum species-coordinated polyoxometalate which contains phosphorus atoms as heteroatoms and in which a chemical species containing divalent platinum (Pt(II)) is introduced into a defect site functions as a photosensitizer and a co-catalyst in a photoreaction in which hydrogen is generated from water by emission of visible light (Non-Patent Literature 1).

CITATION LIST

Non Patent Literature

Non-Patent Literature 1 Dalton Trans., 41, 10021(2012)

SUMMARY OF INVENTION

Technical Problem

It is desirable that a reaction catalyst used for various chemical reactions such as a photocatalyst for allowing hydrogen to be generated from water by emission of visible light have high catalytic activity.

Solution to Problem

An aspect of the present invention relates to a polyoxometalate compound including a metal-substituted polyoxometalate and a counter ion thereof. Another aspect of the present invention relates to a method for producing a polyoxometalate compound. A method according to one aspect of the present invention includes a step of, in a reaction solution containing a polyoxometalate having one or more defect sites and a metal complex having a central metal and an organic ligand, reacting the polyoxometalate with the metal complex to generate a metal-substituted polyoxometalate.

The metal-substituted polyoxometalate includes a polyoxometalate having one or more defect sites, a substituting metal atom introduced into the defect sites, and an organic ligand coordinately bonded to the substituting metal atom. The substituting metal atom is divalent platinum or palladium. The organic ligand may be a bidentate ligand having an aliphatic heterocycle containing two nitrogen atoms coordinately bonded to the substituting metal atom. In the metal-substituted polyoxometalate, one substituting metal atom is introduced into one or more defect sites.

The organic ligand may be two ammonia ligands, two alkylamine ligands having 1 to 3 carbon atoms, or one ethylenediamine ligand, which are coordinately bonded to one central metal or one substituting metal atom. In this case, a metal-substituted polyoxometalate may be generated in the reaction solution at 25° C. or lower.

In the polyoxometalate compound according to another aspect, the metal-substituted polyoxometalate includes a polyoxometalate having one or more defect sites, a first substituting metal atom introduced into the defect site, a first organic ligand coordinately bonded to the first substituting metal atom, a second substituting metal atom introduced into the defect site, and a second organic ligand coordinately bonded to the second substituting metal atom. The first substituting metal atom is a divalent platinum atom and the second substituting metal atom is divalent palladium, or the first substituting metal atom is divalent palladium and the second substituting metal atom is divalent platinum. One first substituting metal atom and one second substituting metal atom are introduced into each of one or more defect sites. Such a binuclear type polyoxometalate compound can be produced by, for example, a method including a step of, in a reaction solution containing a mononuclear type polyoxometalate compound including a metal-substituted polyoxometalate containing a first substituting metal atom and a counter ion thereof, and a metal complex having a central metal, reacting the mononuclear type polyoxometalate compound with the metal complex to generate a binuclear type polyoxometalate compound including the first substituting metal atom and a second substituting metal atom which is the central metal.

Still another aspect of the present invention relates to a reaction catalyst containing any of the above polyoxometalate compounds. For example, the reaction catalyst can exhibit high catalytic activity as a photocatalyst for allowing hydrogen to be generated from water, a hydrogenation reaction catalyst, an exhaust gas purification catalyst, or an electrode catalyst for a fuel cell.

Advantageous Effects of Invention

There are provided a polyoxometalate compound which has high activity as a reaction catalyst used in a chemical reaction such as a photocatalyst for allowing hydrogen to be generated from water and a sintered body hereof. The reaction catalyst according to the present invention is excellent because it is possible to maintain high catalytic activity at a high temperature for a long time therewith.

DESCRIPTION OF EMBODIMENTS

Figure 1:
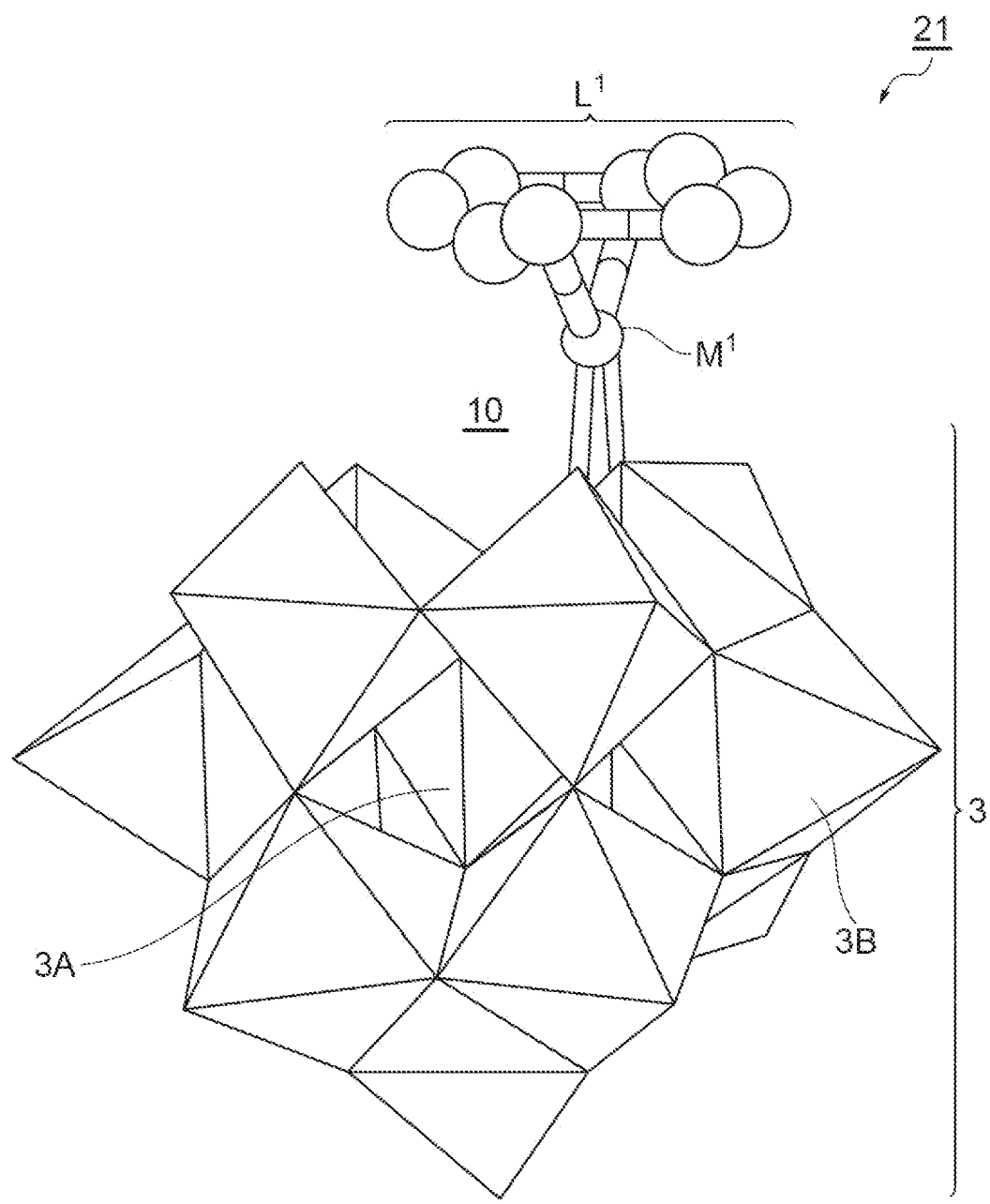
FIG. 1 is a schematic view showing an embodiment of a mononuclear type polyoxometalate compound.

Hereinafter, some embodiments of the present invention will be described in detail. However, the present invention is not limited to the following embodiments.

In this specification, the following abbreviations are used.
Me$_2$ppz: N,N'-dimethylpiperazine
bpy: 2,2'-bipyridine
phen: 1,10-phenanthroline
TMA: tetramethylammonium
Cs—P-1Pt—NH$_3$: Cs$_5$[α-PW$_{11}$O$_{39}${cis-Pt$^{II}$(NH$_3$)$_2$}], or its hydrates
Cs—P-2Pt—NH$_3$: Cs$_3$[α-PW$^{11}$O$_{39}${cis-Pt$^{II}$(NH$_3$)$_2$}$_2$], or its hydrates
TMA-P-1Pt-ppz: [(CH$_3$)$_4$N]$_4$H[α-PW$_{11}$O$_{39}${cis-Pt$^{II}$(Me$_2$ppz)}], or its hydrates
TMA-P-1Pt(NH$_3$)-1Pd(bpy): [(CH$_3$)$_4$N]$_3$[α-PW$_{11}$O$_{39}${Pt$^{II}$(NH$_3$)$_2$}{Pd$^{II}$(bpy)}], or its hydrates
Cs—P-1Pt(NH$_3$)-1Pd(bpy): Cs$_3$[α-PW$_{11}$O$_{39}${Pt$^{II}$(NH$_3$)$_2$}{Pd$^{II}$(bpy)}], or its hydrates
Cs—P-2Pd-bpy: Cs$_3$[α-PW$_{11}$O$_{39}${Pd$^{II}$(bpy)}$_2$].10H$_2$O
TMA-Al-2Pt—NH$_3$: [(CH$_3$)$_4$N]$_4$H[α-AlW$_{11}$O$_{39}${cis-Pt$^{II}$(NH$_3$)$_2$}$_2$)].11H$_2$O
TMA-B-2Pt—NH$_3$: [(CH$_3$)$_4$N]$_4$H[α-BW$_{11}$O$_{39}${cis-Pt$^{II}$(NH$_3$)$_2$}$_2$].9H$_2$O
Cs—Ge-2Pt-bpy: Cs$_4$[α-GeW$_{11}$O$_{39}${cis-Pt$^{II}$bpy)}$_2$].10H$_2$O
Cs—Ge-2Pt-phen: Cs$_{3.5}$H$_{0.5}$[α-GeW$_{11}$O$_{39}${cis-Pt$^{II}$(phen)}$_2$].3H$_2$O
TMA-P-2Pt—NH$_3$: [(CH$_3$)$_4$N]$_3$[α-PW$_{11}$O$_{39}${cis-Pt$^{II}$(NH$_3$)$_2$}$_2$].10H$_2$O
TMA-Si-2Pt—NH$_3$: [(CH$_3$)$_4$N]$_4$[α-SiW$_{11}$O$_{39}${cis-Pt$^{II}$(NH$_3$)$_2$}$_2$].13H$_2$O
TMA-Ge-2Pt—NH$_3$: [(CH$_3$)$_4$N]$_4$[α-GeW$_{11}$O$_{39}${cis-Pt$^{II}$(NH$_3$)$_2$}$_2$].11H$_2$O Polyoxometalate Compound A polyoxometalate compound according to an embodiment includes a metal-substituted polyoxometalate and a counter ion thereof.

Since the metal-substituted polyoxometalate is an anion, the counter ion is generally a cation. The counter ion is not particularly limited, and may be, for example, a metal cation such as Cs$^+$, K$^+$, Na$^+$ and Li$^+$, an alkylammonium cation such as ammonium and tetramethylammonium, a proton (H$^+$), or a combination thereof.

The metal-substituted polyoxometalate includes a polyoxometalate having defect sites, a substituting metal atom introduced into the defect sites and an organic ligand coordinately bonded thereto. The substituting metal atom is typically divalent platinum (Pt(II)) or palladium (Pd(II)).

The polyoxometalate is generally an anion formed by condensing an oxyacid of a transition metal atom and may contain a heteroatom which is an element different from the transition metal atom. A polyoxometalate containing a heteroatom includes, for example, a heteroatom, a plurality of transition metal atoms, and a plurality of oxygen atoms bonded to the heteroatom or the transition metal atom. In this polyoxometalate, generally, a plurality of transition metal atoms are bonded to heteroatoms via an oxygen atom. The number of heteroatoms contained in one molecule of a polyoxometalate compound is generally one. The polyoxometalate compound may form a hydrate.

The polyoxometalate may be, for example, a Keggin type, a Dawson type, an Anderson type or a Waugh type, but in the present embodiment, the polyoxometalate is most typically a Keggin type. A metal-substituted polyoxometalate containing a Keggin type polyoxometalate having one defect site can be represented by, for example, Formula (1):

  (1)

In the formula, X represents a heteroatom, M represents a transition metal atom, M$^1$ represents a substituting metal atom, and L$^1$ represents an organic ligand coordinately bonded to the substituting metal atom M$^1$. n represents an integer of 1 to 10. When M is a tungsten atom (W), n is typically 3, 4 or 5. For example, when X is a phosphorus atom, n is 5, when X is a silicon atom or a germanium atom, n is 6, and when X is a boron atom or an aluminum atom, n is 7. p is 1 or 2, which corresponds to the number of organic ligands L$^1$ coordinately bonded to one substituting metal atom M$^1$. Generally, when the organic ligand L$^1$ is a monodentate ligand, p is 2, and when the organic ligand L is a bidentate ligand, p is 1. The bidentate ligand here is used as a term including a chelate ligand.

For example, the heteroatom can be selected from a phosphorus atom (P), a silicon atom (Si), a germanium atom (Ge), an aluminum atom (Al) and a boron atom (B).

Examples of the transition metal atom include a tungsten atom (W) and a molybdenum atom (Mo). Among these, when the transition metal atom is a tungsten atom, the polyoxometalate compound and its sintered body tend to easily exhibit still higher photocatalytic activity as a reaction catalyst.

FIG. 1 is a schematic view showing an embodiment of a metal-substituted polyoxometalate constituting a polyoxometalate compound. A metal-substituted polyoxometalate 21 shown in FIG. 1 includes a polyoxometalate 3 having one defect site 10, a substituting metal atom M$^1$ introduced into the defect site 10, and an organic ligand L$^1$ coordinately bonded to the substituting metal atom M$^1$. The substituting metal atom M$^1$ is divalent platinum or palladium. As in the embodiment in FIG. 1, a metal-substituted polyoxometalate in which one substituting metal atom is introduced into one defect site and a polyoxometalate compound having the same is sometimes referred to as "mononuclear type" in this specification.

The polyoxometalate 3 is a Keggin type polyoxometalate having one defect site 10 and composed of one base unit 3A formed by a heteroatom and an oxygen atom and 11 base units 3B which are arranged around the base unit 3A and formed by a transition metal atom and an oxygen atom. The base unit 3A is an oxide represented by XO$_4$ (X represents a heteroatom) and has a tetrahedral structure. The base unit 3B is a metal oxide represented by $MO_6$ (M represents a transition metal atom) and has an octahedral structure.

The organic ligand $L^1$ may be a bidentate ligand having an aliphatic heterocycle containing two nitrogen atoms coordinately bonded to one substituting metal atom $M^1$. The aliphatic heterocycle of the bidentate ligand as the organic ligand $L^1$ may contain two nitrogen atoms and two or three carbon atoms continuously arranged between these two nitrogen atoms, as atoms constituting the ring. Examples of organic ligands having such an aliphatic heterocycle include compounds represented by the following Formula (L1), (L2), (L3) or (L4). In these formulae, $R^1$ and $R^2$ each independently represent a hydrogen atom or an alkyl group having 1 to 3 carbon atoms (for example, a methyl group).

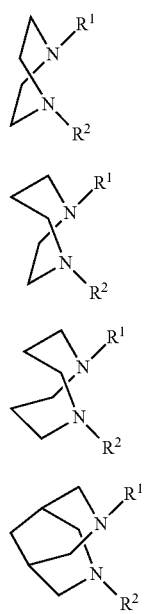

Figure 2:
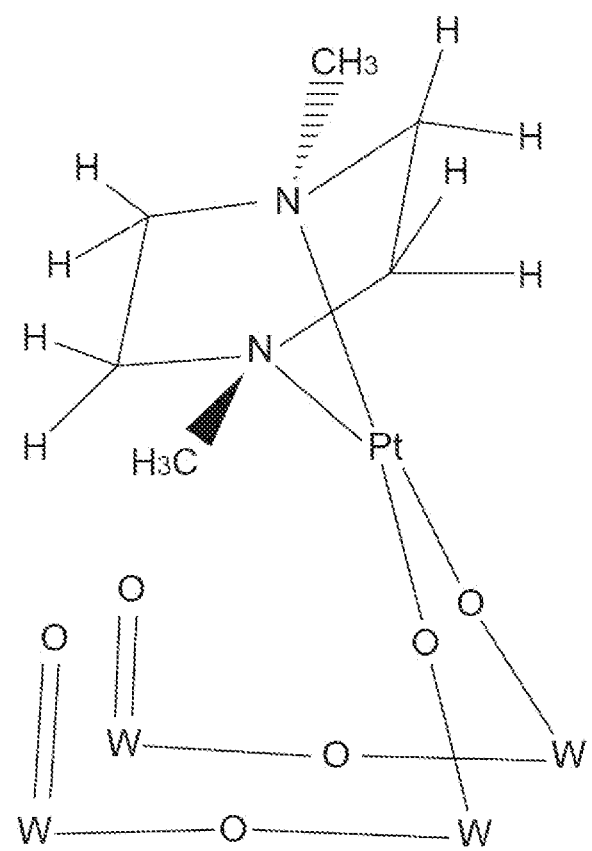
FIG. 2 is a schematic view showing an embodiment of a substituting metal atom introduced into defect sites of a polyoxometalate and an organic ligand coordinately bonded thereto.

FIG. 2 is a schematic view showing an embodiment of substituting metal atoms introduced into defect sites of a polyoxometalate and an organic ligand coordinately bonded thereto. FIG. 2 is an example of a structure estimated when a transition metal atom of the polyoxometalate is tungsten, the substituting metal atom is platinum, and the organic ligand is N,N'-dimethylpiperazine, and the present invention is not limited thereto. In the case of FIG. 2, one platinum atom as a substituting metal atom is bonded to an oxygen atom of a base unit 3B adjacent to the defect site. Two nitrogen atoms in N,N'-dimethylpiperazine as an organic ligand are coordinately bonded to one platinum atom. Since the organic ligand has a bulky aliphatic heterocycle, it is difficult to introduce the second substituting metal atom into the defect site, which is considered to contribute to improving thermal stability of the polyoxometalate compound.

The organic ligand $L^1$ may be two ammonia ligands ($NH_3$), two alkylamine ligands having 1 to 3 carbon atoms or one ethylenediamine ligand. The alkylamine ligands having 1 to 3 carbon atoms may be, for example, methylamine, ethylamine or n-propylamine.

Even if the organic ligand is such a relatively non-bulky compound, for example, as will be described below, when a reaction temperature for generating a metal-substituted polyoxometalate is controlled, the introduction of the second substituting metal atom into the decomposed or defect sites is inhibited, and a mononuclear type metal-substituted polyoxometalate can be obtained with a high yield. In addition, when a second substituting metal atom is additionally introduced into defect sites of a mononuclear type metal-substituted polyoxometalate in which the organic ligand is such a compound, a polyoxometalate compound including a metal-substituted polyoxometalate in which two types of substituting metal atoms are introduced into one defect site can be easily obtained. Such a metal-substituted polyoxometalate in which two substituting metal atoms are introduced into one defect site and a polyoxometalate compound having the same is sometimes referred to as a "binuclear type" in this specification.

The binuclear type metal-substituted polyoxometalate is represented by, for example, Formula (2):

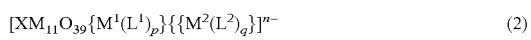

In Formula (2), X, M and p are defined in the same manner as Formula (1). When X is a phosphorus atom, n is 3, when X is a silicon atom or a germanium atom, n is 4, and when X is a boron atom or an aluminum atom, n is 5. $M^1$ and $L^1$ represent a first substituting metal atom and a first organic ligand, respectively, and these are simply referred to as a "substituting metal atom" and an "organic ligand" in the mononuclear type metal-substituted polyoxometalate. $M^2$ represents a second substituting metal atom, $L^2$ represents a second organic ligand, and q is 1 or 2. When the second organic ligand $L^2$ is a monodentate ligand, q is 2, and when the second organic ligand $L^2$ is a bidentate ligand, q is 1. The bidentate ligand here is also used as a term including a chelate ligand.

Figure 3:
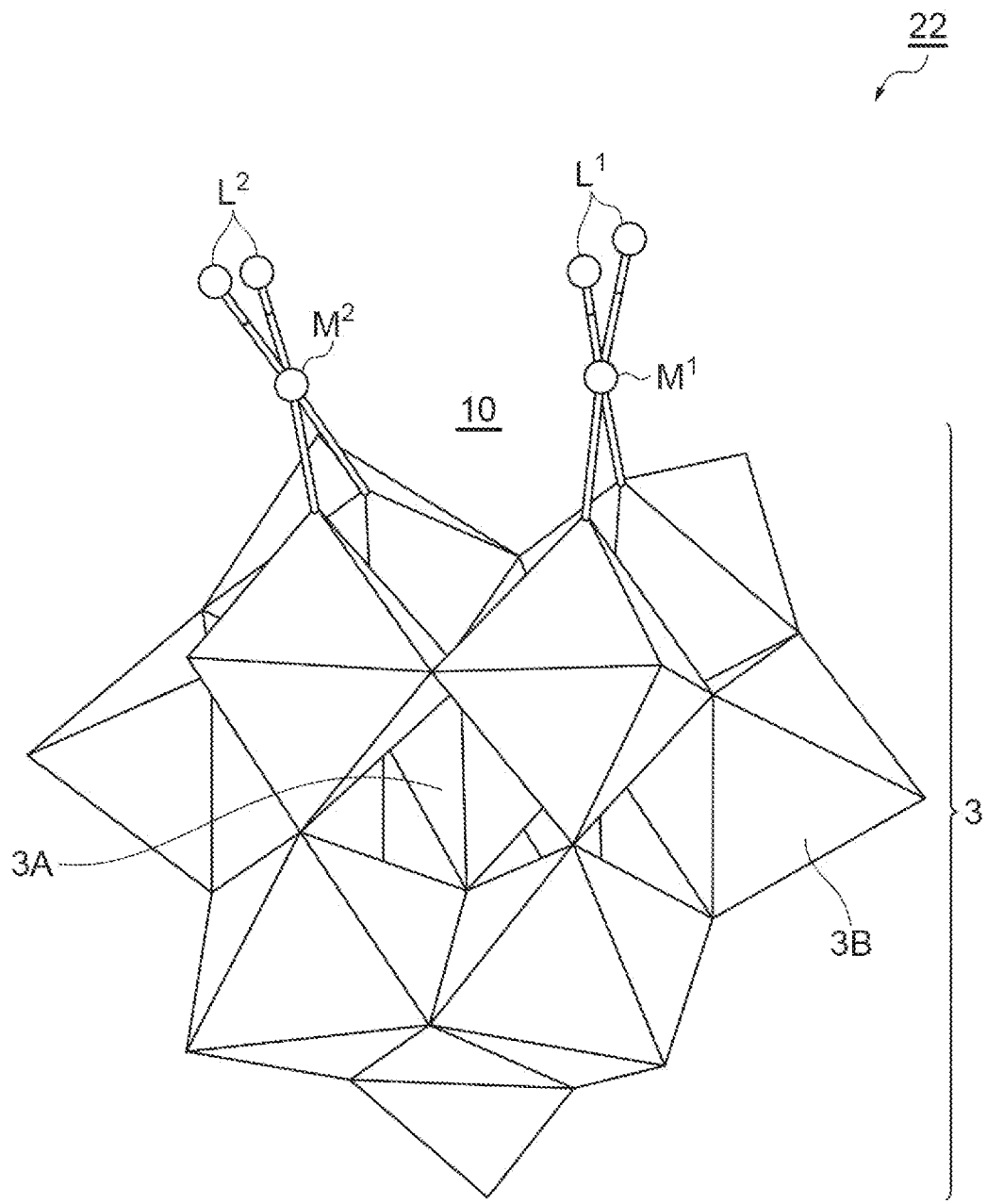
FIG. 3 is a schematic view showing an embodiment of a binuclear type polyoxometalate compound.

FIG. 3 is a schematic view showing an embodiment of a metal-substituted polyoxometalate constituting a binuclear type polyoxometalate compound. A metal-substituted polyoxometalate 22 shown in FIG. 3 includes a polyoxometalate 3 having one defect site 10, a first substituting metal atom $M^1$ introduced into the defect site 10 and a first organic ligand $L^1$ coordinately bonded to the first substituting metal atom $M^1$, a second substituting atom $M^2$ introduced into the defect site 10 and a second organic ligand $L^2$ coordinately bonded to the second substituting metal atom $M^2$. The polyoxometalate 3 of the metal-substituted polyoxometalate 22 has the same configuration as the polyoxometalate 3 in FIG. 1.

When the first substituting metal atom $M^1$ is divalent platinum, the second substituting metal atom $M^2$ is divalent palladium. When the first substituting metal atom $M^1$ is divalent palladium, the second substituting metal atom $M^2$ is platinum. When a combination of two types of substituting metal atoms is introduced into defect sites in this manner, it is possible to obtain a polyoxometalate compound that specifically exhibits still higher catalytic activity and a sintered body thereof.

The first organic ligand $L^1$ in FIG. 3 can be the same compound as the organic ligand $L^1$ in FIG. 1. When the first organic ligand $L^1$ is two ammonia ligands ($NH_3$), two alkylamine ligands having 1 to 3 carbon atoms, or one ethylenediamine ligand, the second substituting metal atom $M^2$ can be particularly easily introduced.

The second organic ligand $L^2$ may the same compound as the first organic ligand $L^1$ or may be any other monodentate ligand or bidentate ligand that can be coordinately bonded to the second substituting metal atom $M^2$. For example, the second organic ligand $L^2$ may be two ammonia ligands ($NH_3$), two alkylamine ligands having 1 to 3 carbon atoms, or one ethylenediamine ligand, or may be a nitrogen-containing heteroaromatic compound such as 2,2'-bipyridine.

The polyoxometalate may have two or more defect sites. When the polyoxometalate has two or more defect sites, one substituting metal atom or two different substituting metal atoms (a first substituting metal atom and a second substituting metal atom) are introduced into each of the defect sites. The polyoxometalate may have two or three defect sites.

Method for Producing a Polyoxometalate Compound

The mononuclear type polyoxometalate compound can be produced by, for example, a method including a step in which, in a reaction solution containing a polyoxometalate having one or more defect sites and a metal complex having a central metal and an organic ligand, the polyoxometalate and the metal complex are reacted to generate a metal-substituted polyoxometalate. Counter ions of the metal-substituted polyoxometalate can be introduced by adding a compound (salt) containing counter ions to the reaction solution after the reaction is completed. Typically, the reaction solution further contains water as a reaction solvent.

When the organic ligand is two ammonia ligands, two alkylamine ligands having 1 to 3 carbon atoms, or one ethylenediamine ligand, the temperature of the reaction solution may be 25° C. or lower or 23° C. or lower. Therefore, it is possible to obtain a mononuclear type metal-substituted polyoxometalate at a high yield while minimizing generation of a binuclear type metal-substituted polyoxometalate into which two substituting metal atoms are introduced and the like. The lower limit of the temperature of the reaction solution may be 10° C. or higher, 15° C. or higher, or 18° C. or higher in order to maintain an appropriate reaction rate. The temperature of the reaction solution may be kept constant or may be varied during the reaction. The reaction time can be adjusted so that the proportion of a desired mononuclear type metal-substituted polyoxometalate increases. For example, the reaction time may be 25 to 30 hours.

When the organic ligand is a bidentate ligand having an aliphatic heterocycle containing two nitrogen atoms, the temperature of the reaction solution may be 5 to 90° C., and the reaction time may be 0.5 to 24 hours.

The polyoxometalate having defect sites for introducing substituting metal atoms can be synthesized by a general method.

The metal complex used for synthesizing a mononuclear type polyoxometalate compound includes a central metal as a substituting metal atom and an organic ligand coordinately bonded to the central metal. The central metal is divalent platinum or palladium, and the organic ligand is as described above. The metal complex may be, for example, a complex represented by the formula: $M^1Cl_2(L^1)_p$. $M^1$, $L^1$ and p are defined in the same manner as Formula (1). Examples of metal complexes including an organic ligand having an aliphatic heterocycle include cis-$[Pt^{II}Cl_2(Me_2ppz)]$. Examples of metal complexes including two ammonia ligands, two alkylamine ligands having 1 to 3 carbon atoms, or one ethylenediamine ligand as an organic ligand include cis-$Pt^{II}(NH_3)_2Cl_2$.

According to the same method as above, the binuclear type polyoxometalate compound can be produced by, for example, a method including a step of obtaining a mononuclear type polyoxometalate compound including: a metal-substituted polyoxometalate containing a first substituting metal atom and a first organic ligand; and a counter ion thereof, and a step in which, in a reaction solution containing the mononuclear type polyoxometalate compound and a metal complex having a central metal, the mononuclear type polyoxometalate compound and the metal complex are reacted to generate a binuclear type polyoxometalate compound containing a first substituting metal atom and a second substituting metal atom. The counter ion of the binuclear type metal-substituted polyoxometalate can be introduced by adding a compound (salt) containing the counter ion to the reaction solution after the reaction is completed. Typically, the reaction solution may further contain water as a reaction solvent.

The metal complex used for synthesizing a binuclear type polyoxometalate compound contains a central metal as a second substituting metal atom and a second organic ligand coordinately bonded to the central metal. As the central metal, whichever of platinum or palladium is different from the first substituting metal atom is selected. The metal complex may be a complex represented by, for example, the formula: $M^2Cl_2(L^2)_q$. $M^2$, $L^2$ and q are defined as in Formula (2). Examples of examples of metal complexes include $Pd^{II}(bpy)Cl_2$.

The temperature of the reaction solution for introducing the second substituting metal atom and the reaction time may be adjusted depending on the reactivity of the metal complex including the second substituting metal atom as a central metal. Typically, the temperature of the reaction solution is 5 to 90° C., and the reaction time is adjusted to 1 second to 10 minutes.

Sintered Body of Polyoxometalate Compound

When the polyoxometalate compound according to the above embodiment is sintered, a sintered body is obtained. The polyoxometalate compound may be sintered in an air atmosphere or an inert gas atmosphere, or in an atmosphere of atmospheric pressure, reduced pressure, or pressurization. In this specification, "sintering a polyoxometalate compound" means that a polyoxometalate compound is heated to such an extent that some chemical properties are irreversibly changed. For example, typically, heating the polyoxometalate compound to 200° C. or higher corresponds to sintering a polyoxometalate compound.

The polyoxometalate compound can be sintered so that at least part of the organic ligand bonded to the substituting metal atom are released. The polyoxometalate compound after the organic ligands are released can exhibit still higher activity as a reaction catalyst. In this regard, the polyoxometalate compound may be sintered until it is substantially free of organic ligands. During sintering, when the polyoxometalate compound is heated to 200° C. or higher, the organic ligands can be easily released. In the same regard, the heating temperature for sintering may be 250° C. or higher. The upper limit of the heating temperature is not particularly limited, but it may be 1000° C. or lower or 550° C. or lower. The heating time for sintering may be appropriately adjusted so that the catalytic activity of the sintered body is improved, and may be, for example, 1 to 20 hours.

The sintered body typically contains a substituting metal atom and a transition metal derived from a polyoxometalate, and has substantially the same molar ratio between substituting metal atoms in the sintered body and transition metal atoms derived from a polyoxometalate as a molar ratio between substituting metal atoms in a polyoxometalate compound and transition metal atoms derived from a polyoxometalate. For example, in the sintered body of a polyoxometalate compound including the metal-substituted polyoxometalate in the above Formula (1), the molar ratio between the substituting metal atom $M^1$ and the transition metal atom M derived from a polyoxometalate may be 1:11.

Reaction Catalyst

The reaction catalyst according to an embodiment includes the oxymetallate compound according to the embodiment described above or a sintered body thereof. The reaction catalyst can exhibit high catalytic activity as a photocatalyst for allowing a photoreaction to proceed by emitting, for example, visible light. In this specification, "photocatalyst" is used as a term including not only a catalyst directly related to the photoreaction but also a photosensitizer. Even if there are no other photosensitizers, the reaction catalyst according to the present embodiment may function as a photocatalyst and a photosensitizer. The reaction catalyst according to the present embodiment may be used as, for example, an oxidation reaction or hydrogenation reaction catalyst, an exhaust gas purification catalyst, or an electrode catalyst for a fuel cell.

EXAMPLES

The present invention will be described below in more detail with reference to examples. However, the present invention is not limited to these examples.

1. Measurement Method 1-1 NMR Spectrum

The NMR spectrum of each nuclide was measured with an FT NMR device ECA-600 (commercially available from JEOL Ltd.).

1-2. Elemental Analysis

C, H and N were quantified with a Flash FA (commercially available from Thermo Electron Co., Ltd.). P, Pt and K were quantified with Optima 2100DV (commercially available from PerkinElmer Co., Ltd.).

1-3. Infrared Absorption Spectrum

The infrared absorption spectrum was measured with Spectrum 100 FTIR (commercially available from PerkinElmer Co., Ltd.).

1-4. Thermogravimetric-Differential Thermal Analysis (TG/DTA)

Thermogravimetric-differential thermal analysis was performed with a differential thermal balance Thermo plus EVO2 TG-DTA 81205Z (commercially available from Rigaku Corporation).

2. Platinum-Substituted Polyoxometalate Compound (Mononuclear Type)

2-1. Cs—P-1Pt—$NH_3$($Cs_5[\alpha$-$PW_{11}O_{39}\{$cis-$Pt^{II}(NH_3)_2\}]\cdot 6H_2O$) Synthesis Cis-diamminedichloroplatinum (II) (cis-$Pt^{II}(NH_3)_2Cl_2$; 0.0604 g; 0.201 mmol; MW: 300.05) was dissolved in 150 mL of water at room temperature. A solution obtained by dissolving $K_7[PW_{11}O_{39}]\cdot 10H_2O$ (0.3172 g; 0.101 mmol; MW: 3131.031) in 15.0 mL of water at room temperature was added thereto, and the resulting reaction solution was stirred in a water bath at 20±2° C. for 27 hours. The reaction solution was moved to an ice bath, and, a solution obtained by dissolving cesium chloride (0.7531 g; 4.47 mmol; MW: 168.36) in 3 mL of water to was added thereto while stirring. The reaction solution was additionally stirred in an ice bath for 20 minutes, 540 mL of ethanol was then added thereto, and the reaction solution was stirred for 10 minutes. The generated precipitate was collected with a membrane filter. The collected precipitate was suction-dried and then freeze-dried to obtain a product containing Cs—P-1Pt—$NH_3$ (yellow powder, yield 0.3,547 g).

Figure 4:
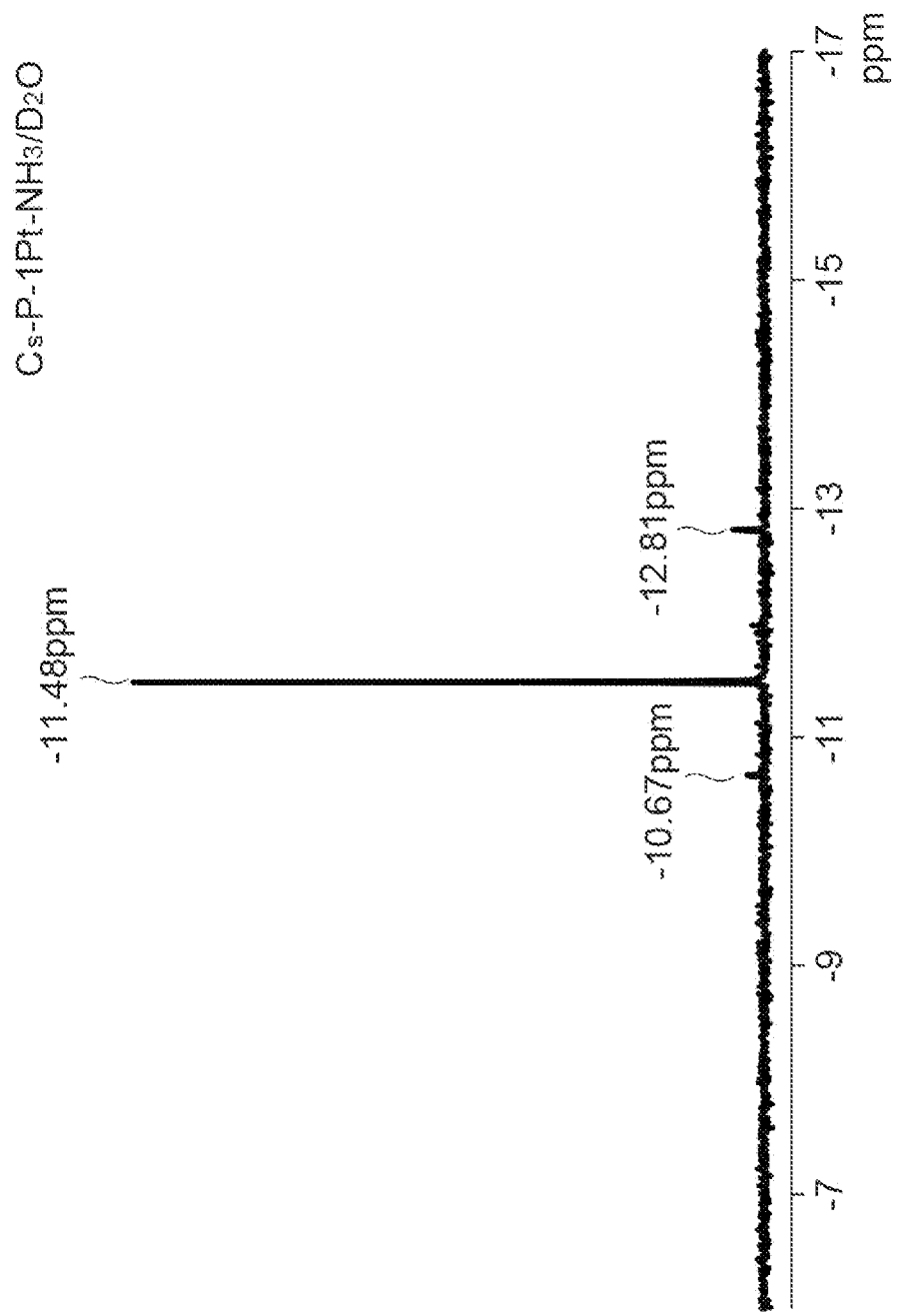
FIG. 4 shows a $^{31}$P NMR spectrum of Cs—P-1Pt-NH$_3$.

The $^{31}P$ NMR spectrum of the product was measured using $H_3PO_4$ as a standard substance in $D_2O$. FIG. 4 shows $^{31}P$ NMR spectrums of the product. Signals attributed to Cs—P-1Pt—$NH_3$ were observed at −11.48 ppm and a few signals attributed to Cs—P-2Pt—$NH_3$ were observed at −12.81 ppm and a few signals attributed to $[\alpha$-$PW_{11}O_{39}]^{7-}$ were observed at −10.67 ppm. The abundance ratio of $[\alpha$-$PW_{11}O_{39}]^{7-}$:Cs—P-1Pt—$NH_3$:Cs—P-2Pt—$NH_3$ obtained from the integrated intensity of the signals was 0.06:1.00:0.02. As a result of elemental analysis, it was confirmed that, since the molar ratio of P:Pt was about 1:1, Cs—P-1Pt—$NH_3$ was obtained with high purity. In addition, in the infrared absorption spectrum (KBr) of the product, absorption was confirmed at 1091, 1045, 952, 894, 862, 807, 760, and 730 $cm^{-1}$, which was different from the infrared absorption spectrum of Cs—P-2Pt—$NH_3$($Cs_3[\alpha$-$PW_{11}O_{39}\{$cis-$Pt(NH_3)_2\}_2]\cdot 8H_2O$) and $K_7[\alpha$-$PW_{11}O_{39}]\cdot 13H_2O$. In addition, absorption derived from $NH_3$ was observed near 1,346 $cm^{-1}$.

Study of Reaction Conditions

Figure 5:
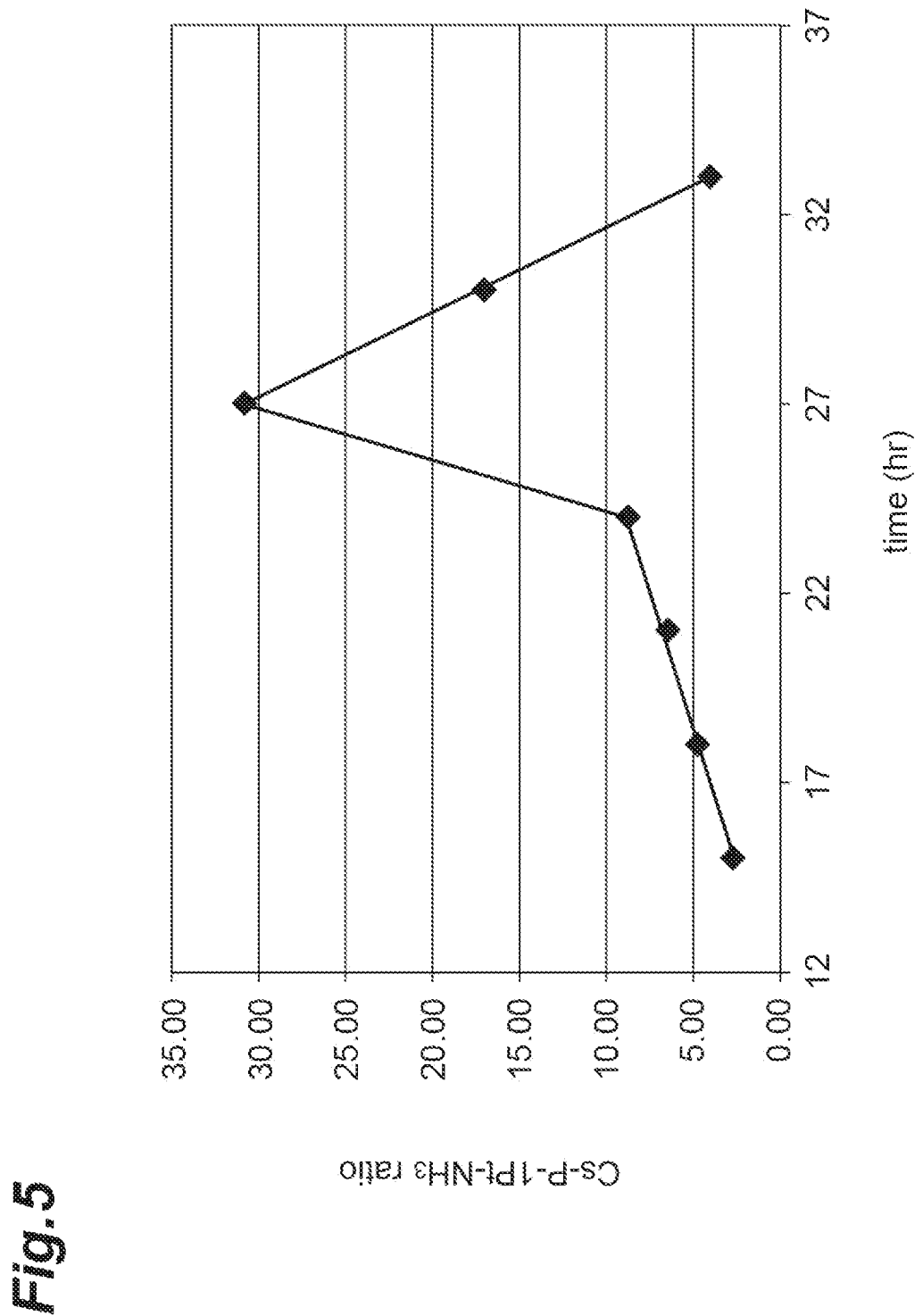
FIG. 5 is a graph showing the relationship between the ratio of Cs—P-1Pt-NH$_3$ and a reaction time.

In the same manner as above, cis-$Pt^{II}(NH_3)_2Cl_2$ and $K_7[PW_{11}O_{39}]$ were reacted at a reaction temperature of 20° C. and a reaction time of 15 hours, 18 hours, 21 hours, 24 hours, 27 hours, 30 hours or 33 hours. $^{31}P$ NMR of the product was measured, and the integrated intensity ratio of the signal of Cs—P-1Pt—$NH_3$ to the signal of $[\alpha$-$PW_{11}O_{39}]^{7-}$ was determined as the ratio of Cs—P-1Pt—$NH_3$. FIG. 5 is a graph showing the relationship between the ratio of the Cs—P-1Pt—$NH_3$ and the reaction time. It was confirmed that, when the reaction temperature was 20° C. and the reaction time was about 25 to 30 hours, a mononuclear Cs—P-1Pt—$NH_3$ was obtained with a particularly high yield.

When the reaction was performed in the same manner at a reaction temperature of 30° C., $[PW_{11}O_{39}]^{7-}$:Cs—P-1Pt—$NH_3$ was 1.00:0.92 after 6 hours, and the ratio of binuclear Cs—P-2Pt—$NH_3$ was higher than the ratio of Cs—P-1Pt—$NH_3$ after 27 hours. Based on these results, it can be understood that it was appropriate to set the reaction temperature to about 25° C. or lower, because it was possible to obtain a mononuclear component with a high yield.

2-2. TMA-P-1Pt-ppz($[(CH_3)_4N]_4H[PW_{11}O_{39}\{$cis-$Pt^{II}(Me_2ppz)\}]\cdot 5H_2O$)

Cis-$[Pt^{II}Cl_2(Me_2ppz)]$ (0.0758 g; 0.2 mmol MW: 380.176) was dissolved in 35 mL of water at 50° C. The resulting solution was added to a solution obtained by dissolving $K_7[PW_{11}O_{39}]\cdot 13H_2O$ (0.643 g; 0.2 mmol; MW: 3185.08) in 5 mL of water at room temperature. The resulting reaction solution was stirred at 25° C. for 24 hours. Solid $(CH_3)_4NBr$ (1.035 g; 9.4 mmol) was added thereto, and the reaction solution was additionally stirred at 25° C. for 24 hours. The precipitated yellow precipitate was collected with a membrane filter and washed with ethanol. At this point, 0.437 g of a crude product was obtained. The crude product was dissolved in 20 mL of water at 50° C. and the solution was left in a refrigerator overnight. The precipitated yellow precipitate was collected with a membrane filter, and the collected precipitate was washed with ethanol to obtain a product containing TMA-P-1Pt-ppz (yield 0.1447 g). Based on the result of the following elemental analysis, it was confirmed that the mononuclear TMA-P-1Pt-ppz was obtained mostly selectively.

Elemental Analysis:

found: C, 7.78; H, 1.89; N, 2.48; P, 0.98; Pt, 5.76; K, <0.1%.

Calculations for $[(CH_3)_4N]_4H[PW_{11}O_{39}\{Pt(Me_2ppz)\}]\cdot 5H_2O=H_{73}C_{22}N_6Pt_1O_{44}P_1W_{11}$ (MW: 3374.129): C, 7.83; H, 2.18; N, 2.49; P, 0.92; Pt, 5.78; K, 0%.

Thermogravimetric-Differential Thermal Analysis (TG/DTA)

As a result of TG/DTA analysis of the product (TMA-P-1Pt-ppz) under an atmospheric atmosphere, a weight loss of 2.90% which was almost equivalent to 5 molecules of water was observed at a temperature of lower than 92.5° C. In addition, a weight loss of 13.03% was observed with two exothermic peaks at 273.8° C. and 374.9° C., and this was thought to correspond to 4 molecules of $[(CH_3)_4N]^+$ and one molecule of $Me_2ppz$.

Infrared Absorption Spectrum (KBr)

Figure 6A:
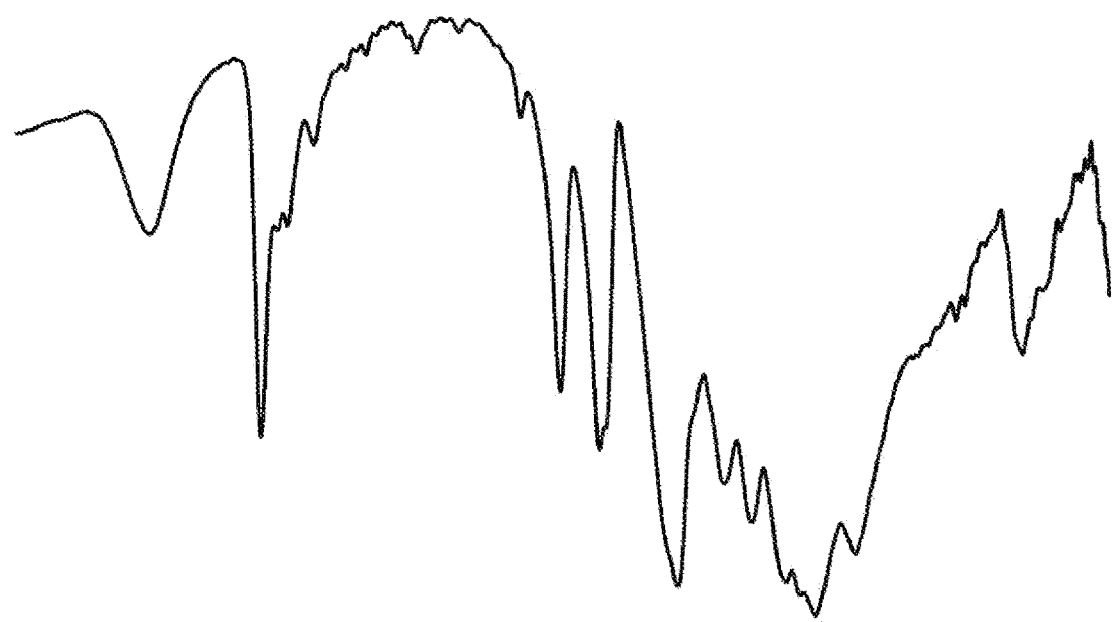
FIGS. 6(a) and 6(b) show infrared absorption spectrums of TMA-P-1Pt-ppz and K$_7$[PW$_{11}$O$_{39}$].13H$_2$O.
Figure 6B:
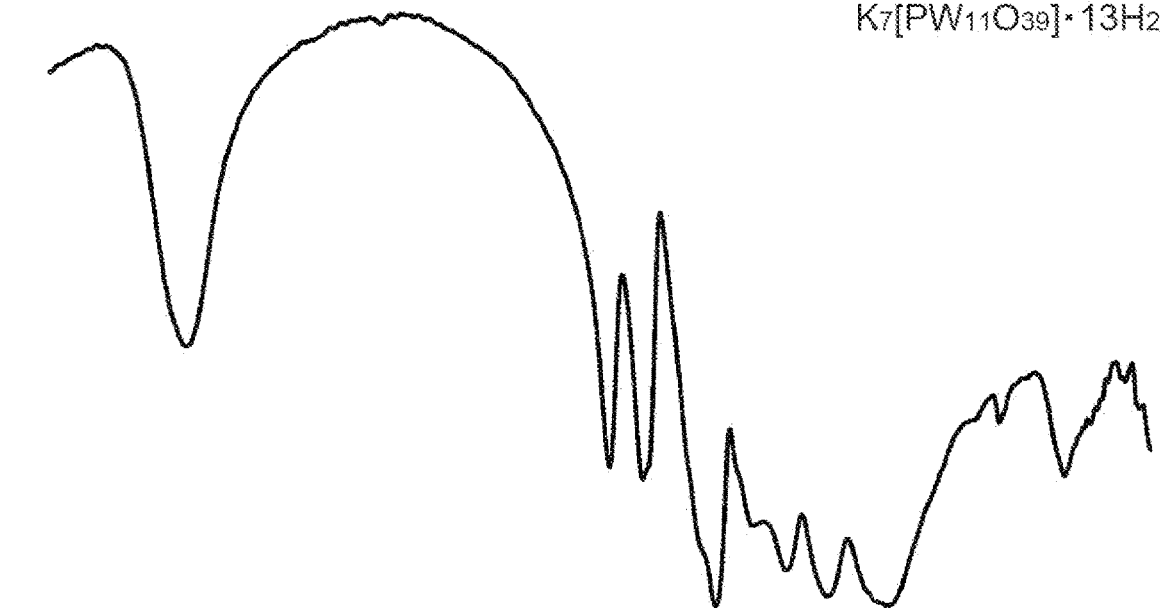

FIG. 6 shows infrared absorption spectrums of the product (TMA-P-1Pt-ppz) and $K_7[PW_{11}O_{39}]\cdot 13H_2O$. FIG. 6(a) shows TMA-P-1Pt—$NH_3$, and FIG. 6(b) shows $K_7[PW_{11}O_{39}]\cdot 13H_2O$. TMA-P-1Pt-ppz exhibited absorption derived from $[(CH_3)_4N]^+$ and $Me_2ppz$ near 1,488 cm$^{-1}$.

NMR Spectrum

Figure 7A:
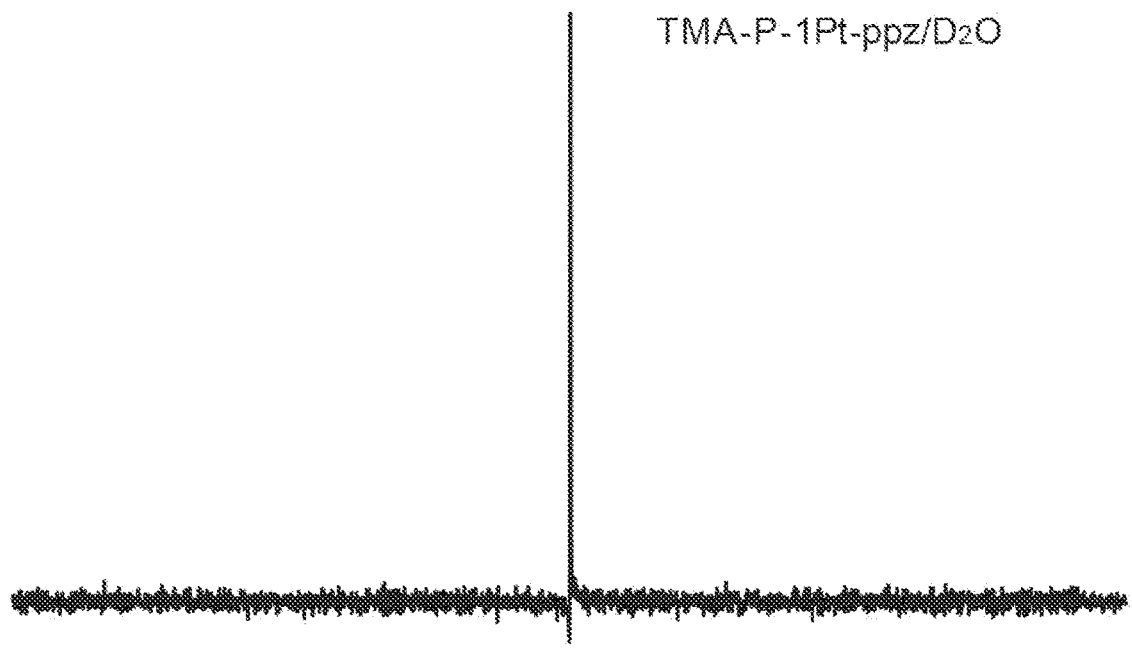
FIGS. 7(a) and 7(b) show $^{31}$P NMR spectrums of TMA-P-1Pt-ppz.
Figure 7B:
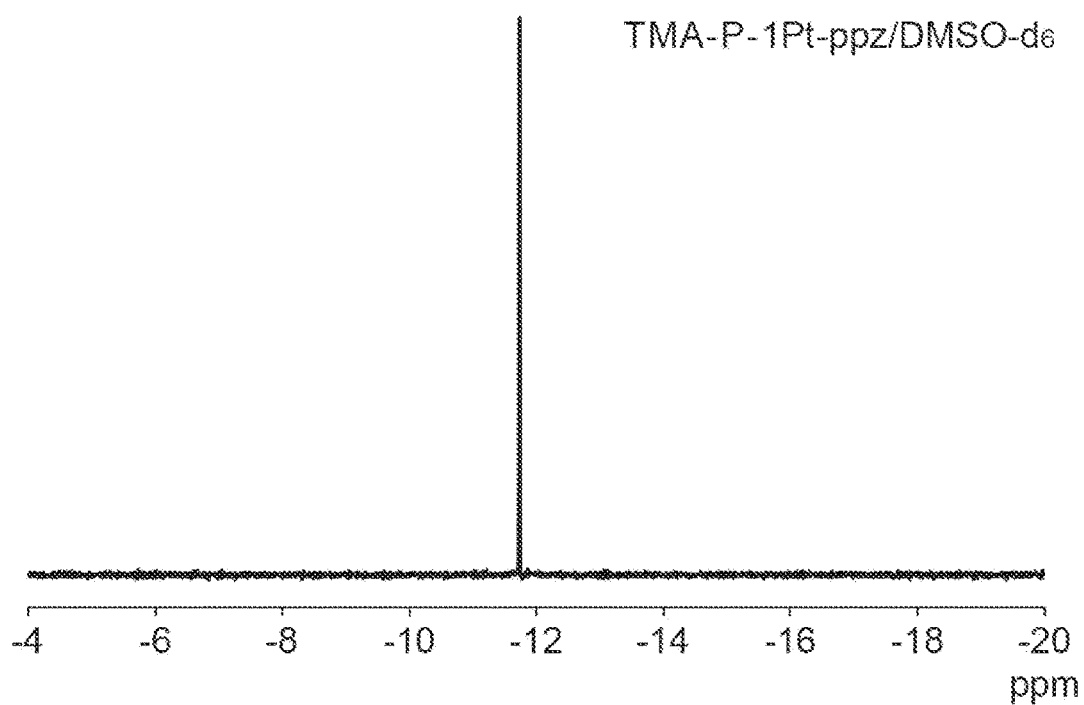

FIG. 7 shows a $^{31}P$ NMR spectrum of TMA-P-1Pt-ppz. FIG. 7(a) shows measurement data in $D_2O$ and FIG. 7(b) shows measurement data in DMSO-$d_6$. The NMR spectrum data including other nuclides are shown below.

$^{13}C$ NMR (DMSO-$d_6$, 23.4° C.): δ57.7 ($[(CH_3)_4N]^+$), 50.9 and 51.4 (—$CH_2CH_2$— groups in $Me_2ppz$), 21.7 (($CH_3)_2ppz$)

$^{31}P$ NMR: ($D_2O$, 21.3° C.): δ-12.03

$^{31}P$ NMR: (DMSO-$d_6$, 22.6° C.): δ-11.75

$^{195}Pt$ NMR (DMSO-$d_6$, 20.7° C.): δ-1326

Figure 8A:
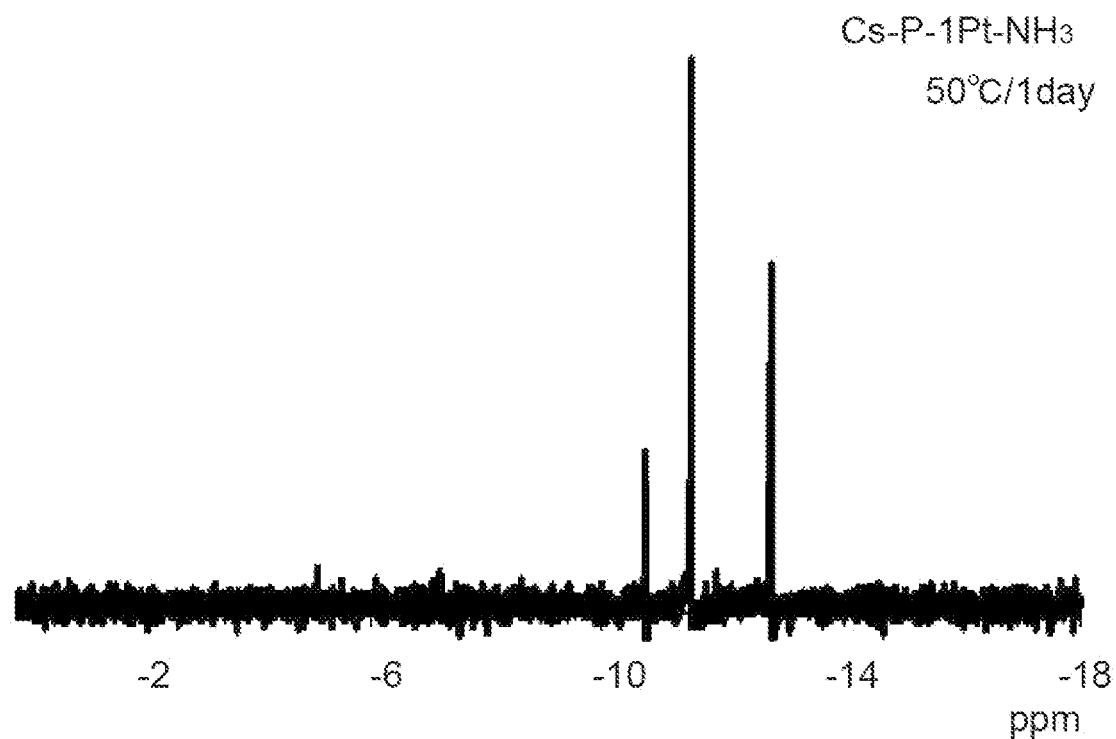
FIGS. 8(a) and 8(b) show $^{31}$P NMR spectrums of Cs—P-1Pt-NH$_3$ and TMA-P-1Pt-ppz after being left at 50±2° C. for 24 hours.
Figure 8B:
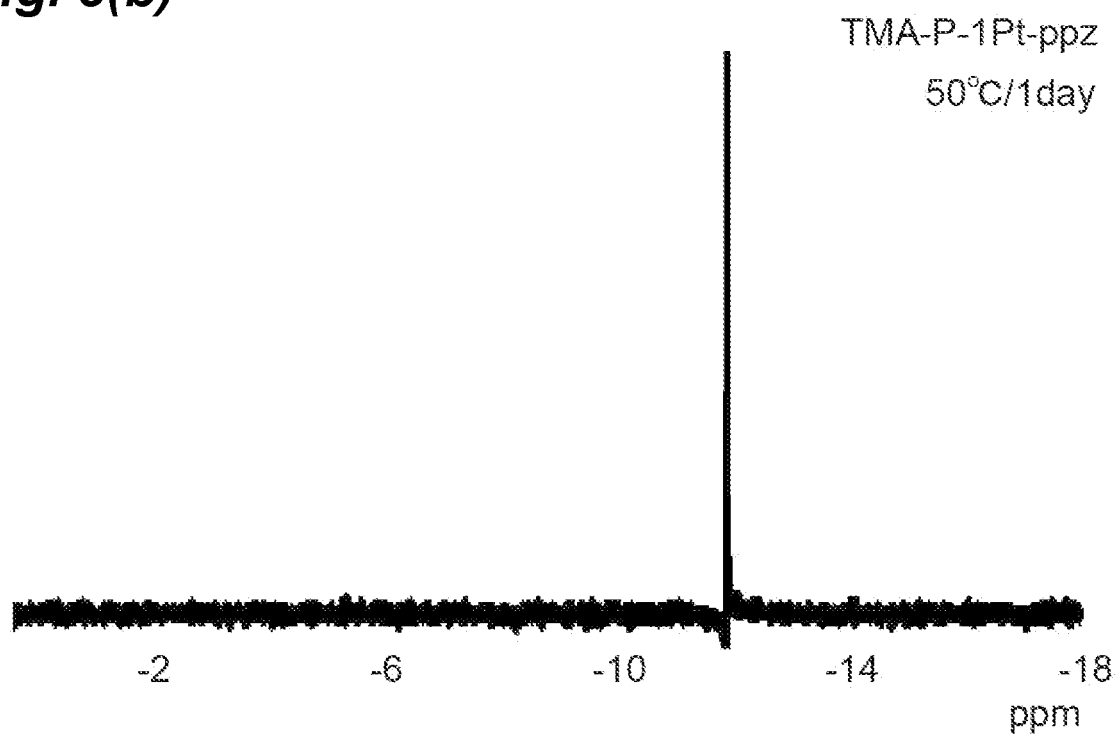

Stability Evaluation 10.5 mg of Cs—P-1Pt—$NH_3$ and 4.4 μmol of TMA-P-1Pt-ppz were dissolved in 600 μL of $D_2O$ respectively. The resulting solution was left in an environment at 50±2° C. FIG. 8 shows $^{31}P$ NMR spectrums of the polyoxometalate compounds after being left at 50±2° C. for 1 day. In the case of Cs—P-1Pt—$NH_3$ in FIG. 8(a), signals of $[PW_{11}O_{39}]^{7-}$ and Cs—P-2Pt—$NH_3$ appeared, and this suggested that decomposition of Cs—P-1Pt—$NH_3$ gradually proceeded. On the other hand, in the case of TMA-P-1Pt-ppz in FIG. 8(b), almost no decomposition was observed. It was confirmed that TMA-P-1Pt-ppz did not substantially decompose even after being left at 50±2° C. for 7 days and had high thermal stability.

3. Platinum-Substituted Polyoxometalate Compound (Binuclear)

3-1. TMA-Al-2Pt—$NH_3$($[(CH_3)_4N]_4H[\alpha$-$AlW_{11}O_{39}$\{cis-$Pt^{II}(NH_3)_2$\}$_2]\cdot 11H_2O$)

$K_9[\alpha$-$AlW_{11}O_{39}]\cdot 13H_2O$ (0.665 g; 0.20 mmol) was added to a solution obtained by dissolving cis-$Pt^{II}(NH_3)_2Cl_2$ (0.120 g; 0.40 mmol) in 140 mL of water. When the obtained reaction solution was stirred at 60° C. for 2 hours, a yellow precipitate was precipitated. The precipitate was removed with a membrane filter, and solid $(CH_3)_4NCl$ (8.772 g: 80 mmol) was added to the filtrate. After stirring at 25° C. for 3 days, the precipitated yellow precipitate was collected with a membrane filter. The obtained crude product (0.347 g) was dissolved in 10.4 mL of water at 70° C. and purified by steam diffusion at 25° C. using ethanol. After being left for 5 days, yellow crystals were collected with a membrane filter and washed with 10 mL of ethanol. This crystallization was performed twice to obtain 0.1110 g of yellow single crystals. Based on the result of analysis including the following elemental analysis, it was confirmed that a binuclear TMA-Al-2Pt—$NH_3$ was obtained.

Elemental Analysis:

found: C, 5.37; H, 2.16; N, 3.07; Al, 0.65; Pt, 10.53; K, <0.1%.

Calculations for $[(CH_3)_4N]_4H[AlW_{11}O_{39}$\{cis-Pt$(NH_3)_2$\}$_2]\cdot xH_2O$ (x=11)=$C_{16}H_{83}N_8Pt_2O_{50}Al_1W_{11}$: C, 5.30; H, 2.31; N, 3.09; Al, 0.74; Pt, 10.76; K, 0%.

3-2. TMA-B-2Pt—$NH_3$($[(CH_3)_4N]_4H[\alpha$-$BW_{11}O_{39}$\{cis-$Pt^{II}(NH_3)_2$\}$_2]\cdot 9H_2O$)

$K_8H[\alpha$-$BW_{11}O_{39}]\cdot 16H_2O$ (0.661 g; 0.20 mmol) was dissolved in 40 mL of water. This solution was added to a solution obtained by dissolving cis-$Pt^{II}(NH_3)_2Cl_2$ (0.121 g; 0.40 mmol) in 150 mL of water. When the resulting reaction solution was stirred at 25° C. for 10 days, a yellow precipitate was precipitated. The precipitate was removed with a membrane filter, solid $(CH_3)_4NCl$ (3.52 g: 32.1 mmol) was added to the filtrate, and the filtrate was stirred for 2 hours while cooling with ice. Then, the precipitated yellow precipitate was collected with a membrane filter, and washed with a small amount of ethanol. The obtained crude product (0.5458 g) was dissolved in 25 mL of water at 70° C. and left in a refrigerator for 7 to 10 days. The precipitated yellow crystals were collected with a membrane filter and washed with a small amount of ethanol. Purification by this crystallization was performed twice to obtain 0.2255 g of a crystal product.

Based on the result of analysis including the following elemental analysis, it was confirmed that a binuclear TMA-Al-2Pt—$NH_3$ was obtained.

Elemental Analysis:

found: C, 5.32; H, 2.02; N, 3.07; B, 0.29; Pt, 10.84; K, <0.1%

Calculations for $[(CH_3)_4N]_4H[\alpha$-$BW_{11}O_{39}$\{cis-Pt$(NH_3)_2$\}$_2]\cdot xH_2O$ (x=9)=$C_{16}H_{79}N_8Pt_2O_{48}B_1W_{11}$: C, 5.38; H, 2.23; N, 3.13; B, 0.30; Pt, 10.91; K, 0%

3-3. Cs—Ge-2Pt-bpy($Cs_4[\alpha$-$GeW_{11}O_{39}$\{cis-$Pt^{II}(bpy)$\}$_2]\cdot 10H_2O$)

Cis-$Pt^{II}(bpy)_2Cl_2$ (0.0844 g; 0.20 mmol) was added to a solution obtained by dissolving $K_6Na_2[\alpha$-$GeW_{11}O_{39}]\cdot 12H_2O$ (0.3286 g; 0.10 mmol) in 200 mL of water. The resulting reaction solution was stirred at 90° C. for 2 hours and solid CsCl (2.08 g; 12 mmol) was then added to the reaction solution, and the reaction solution was stirred at 25° C. for 1 day. The precipitated yellow precipitate was collected with a membrane filter, and washed with a small amount of ethanol. The obtained crude product (0.3823 g) was dissolved in 90 mL of water at 80° C. and the solution was left in a refrigerator at about 5° C. for 9 days. The precipitated yellow precipitate was collected with a membrane filter to obtain 0.2861 g of a product. Based on the result of analysis including the following elemental analysis, it was confirmed that a binuclear Cs—Ge-2Pt-bpy was obtained.

Elemental Analysis:

found: C, 5.91; H, 0.56; N, 1.36; Ge, 1.74; Pt, 9.48; Cs, 12.5; K, <0.1; Na, <0.1%

Calculations for $Cs_4$ $[GeW_{11}O_{39}$\{Pt(bpy)\}$_2]\cdot xH_2O$ (x=10)=$C_{20}H_{36}Cs_4N_4Pt_2O_{49}Ge_1W_{11}$: C, 5.81; H, 0.88; N, 1.36; Ge, 1.76; Pt, 9.44; Cs, 12.86; K, 0; Na, 0%

3-4. Cs—Ge-2Pt-phen($Cs_{3.5}H_{0.5}[\alpha$-$GeW_{11}O_{39}$\{cis-$Pt^{II}(phen)$\}$_2]\cdot 3H_2O$)

Cis-$Pt^{II}(phen)_2Cl_2$ (0.0905 g; 0.20 mmol) was added to a solution obtained by dissolving $K_6Na_2[\alpha$-$GeW_{11}O_{39}]\cdot 12H_2O$ (0.3290 g; 0.10 mmol) in 200 mL of water. The resulting reaction solution was stirred at 90° C. for 8 hours and solid CsCl (2.08 g; 12 mmol) was then added to the reaction solution, and the reaction solution was stirred at 25° C. for 2 days. The precipitated yellow precipitate was collected with a membrane filter, and washed with a small amount of ethanol. The obtained crude product (0.3626 g) was dissolved in 90 mL of water at 90° C. and the solution was left in a refrigerator at about 5° C. for 5 days. The precipitated yellow crystals were collected with a membrane filter to obtain 0.2248 g of a product. Based on the result of analysis including the following elemental analysis, it was confirmed that a binuclear Cs—Ge-2Pt-phen was obtained.

Elemental Analysis:
found: C, 7.04; H, 0.55; N, 1.35; Ge, 1.75; Pt, 9.53; Cs, 12.0; K, <0.1; Na, <0.1%
Calculations for $Cs_{3.5}H_{0.5}[GeW_{11}O_{39}\{Pt(phen)\}_2] \cdot xH_2O$ (x=3)=$C_{24}H_{22.5}Cs_{3.5}N_4Pt_2O_{42}Ge_1W_{11}$: C, 7.23; H, 0.57; N, 1.40; Ge, 1.82; Pt, 9.78; Cs, 11.66; K, 0; Na, 0%

4. Platinum-Palladium Substituted Polyoxometalate Compound (Binuclear Type)

4-1. TMA-P-1Pt($NH_3$)-1Pd(bpy)($[(CH_3)_4N]_3[\alpha\text{-}PW_{11}O_{39}\{Pt^{II}(NH_3)_2\}\{Pd^{II}(bpy)\}]$)

0.1826 g of Cs—P-1Pt—$NH_3$ (MW: 3678.95, 0.050 mmol) was dissolved in 50 mL of distilled water to obtain a light yellow transparent solution. This solution was added to a light yellow transparent solution obtained by dissolving 0.0163 g of $Pd^{II}(bpy)Cl_2$ (MW: 333.51, 0.049 mmol) in 50 mL of distilled water in a hot water bath at 90° C., in an ice bath. The obtained reaction solution was stirred for 3 minutes and 3.948 g (MW: 109.60, 36 mmol) of tetramethylammonium chloride was then added to precipitate a white yellow precipitate. The precipitate was collected with a membrane filter and washed with ethanol. The washed precipitate was suction-dried, and then freeze-dried to obtain a product containing TMA-P-1Pt($NH_3$)-1Pd(bpy) (yield 0.0733 g).

Figure 9:
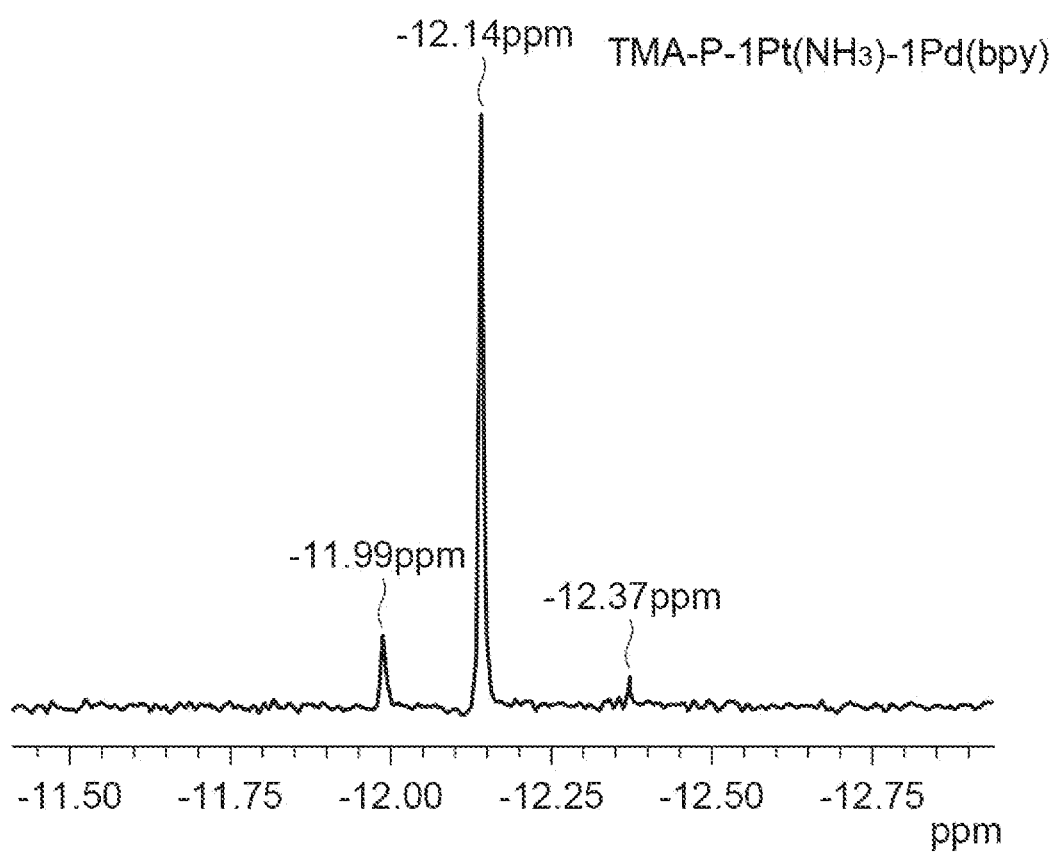
FIG. 9 shows a $^{31}$P NMR spectrum of TMA-P-1Pt(NH$_3$)-1Pd(bpy).

FIG. 9 shows a $^{31}P$ NMR spectrum of the product. A signal derived from TMA-P-1Pt($NH_3$)-1Pd(bpy) was observed at −12.14 ppm. In addition, a signal of $[PW_{11}O_{39}\{Pd(bpy)\}_2]^{3-}$ was observed at −11.99 ppm and a signal of $[PW_{11}O_{39}\{Pt(NH_3)_2\}_2]^{3-}$ was observed at −12.37 ppm. The integrated intensity ratio between these signals was $[PW_{11}O_{39}\{Pd(bpy)\}_2]^{3-}$: TMA-P-1Pt($NH_3$)-1Pd(bpy): $[PW_{11}O_{39}\{Pt(NH_3)_2\}_2]^{3-}$=1.00:8.25:0.22. The purity of TMA-P-1Pt($NH_3$)-1Pd(bpy) calculated from the result of the following elemental analysis was 81%.

Elemental Analysis
found: P 0.72%; Pt 5.03%; Pd 3.93%
calculated for $[(CH_3)_4N]_3[PW_{11}O_{39}\{Pt(NH_3)_2\}\{Pd(N_2C_{10}H_8)\}_2]_{0.81}[PW_{11}O_{39}\{Pt(NH_3)_2\}_2]_{0.01} \cdot 2H_2O$:P 0.90%; Pt 4.72%; Pd 3.63%=$C_{23.7}H_{54.34}N_7O_{41}P_1Pd_{1.17}Pt_{0.83}W_{11}$(MW 3433.096)

3-2. Cs—P-1Pt($NH_3$)-1Pd(bpy)($[Cs_3[\alpha\text{-}PW_{11}O_{39}\{Pt^{II}(NH_3)_2\}\{Pd^{II}(bpy)\}]$)

0.1839 g of Cs—P-1Pt—$NH_3$ (MW: 3678.95, 0.050 mmol) was dissolved in 50 mL of distilled water to obtain a light yellow transparent solution. This solution was added to a light yellow transparent solution obtained by dissolving 0.0167 g of $Pd^{II}(bpy)Cl_2$ (MW: 333.51, 0.051 mmol) in 50 mL of distilled water in a hot water bath at 90° C., in an ice bath. The resulting reaction solution was stirred for 3 minutes and 3.800 g (MW: 168.36, 22.6 mmol) of cesium chloride was then added to precipitate a white yellow precipitate. The precipitate was collected with a membrane filter and washed with ethanol. The washed precipitate was suction-dried, and then freeze-dried to obtain a product containing Cs—P-1Pt($NH_3$)-1Pd(bpy) (yield 0.1284 g).

The $^{31}P$ NMR spectrum of the product was measured in dimethyl sulfoxide (DMSO)-$d_6$. In the obtained $^{31}P$ NMR spectrum, a signal derived from Cs—P-1Pt($NH_3$)-1Pd(bpy) was observed at −12.15 ppm, and a signal of $PW_{11}O_{39}\{Pd(bpy)_2\}_2]^{3-}$ was observed at −12.00 ppm. The integrated intensity ratio between these signals was $[PW_{11}O_{39}\{Pd(bpy)\}_2]^{3-}$:Cs—P-1Pt($NH_3$)-1Pd(bpy)=1.00:11.98.

5. Photocatalytic Activity
5-1. Polyoxometalate Compound
Test 1

Each polyoxometalate compound in an amount containing 0.2 to 3.0 μmol of platinum atoms, 2.5 μmol of eosin Y, 2.5 μmol of $K_5SiW_{11}\{Al(OH)_2\}O_{39}] \cdot 7H_2O$, 50 mg of $TiO_2$ particles (anatase:rutile=80:20), 10 mL of water, and 100 mM of triethanolamine (TEA) were mixed to prepare a reaction solution for a photocatalytic reaction in which hydrogen was generated from water. The amount of the polyoxometalate compound was adjusted to an amount corresponding to 0.2 to 0.6 μmol of platinum atoms shown in Table 1.

Light of 440 nm or more was emitted to the reaction solution in an environment at 25° C. and the amount of hydrogen generated by the photocatalytic reaction was quantified. The amount of $H_2$ generated after 1 hour and the turnover number (TON, 2×(amount of $H_2$ generated (mol)/amount of Pt atoms (mol)) as an index of the photocatalytic activity were measured. For comparison, the photocatalytic activity of Cs—P-2Pd-bpy which was a binuclear component of palladium synthesized by the same method as above and commercially available platinum black was evaluated in the same manner.

TABLE 1

| Catalyst (μmol of Pt) | Amount of $H_2$ generated (μmol) | TON |
|---|---|---|
| TMA—P—1Pt-ppz (0.6) | 188 | 628 |
| Cs—P—1Pt—$NH_3$ (0.6) | 216 | 720 |
| TMA—P—1Pt($NH_3$)—1Pd(bpy) (0.6) | 313 | 1060 |
| Cs—P—2Pt—$NH_3$ (0.2) | 9 | 93 |
| Cs—P—2Pd-bpy (0.6) | 32 | 111 |
| Platinum black (3.0) | 18 | 12 |

As shown in Table 1, TMA-P-1Pt-ppz and Cs—P-1Pt—$NH_3$ which were a mononuclear polyoxometalate compound had a significantly higher turnover number than the binuclear Cs—P-2Pt—$NH_3$. In addition, TMA-P-1Pt($NH_3$)-1Pd(bpy) which was a platinum-palladium binuclear component showed the turnover number that was more significantly improved.

Test 2

Photocatalytic activities of TMA-Al-2Pt—$NH_3$, TMA-B-2Pt—$NH_3$, Cs—Ge-2Pt-bpy, and Cs—Ge-2Pt-phen, and TMA-P-2Pt-$NH_3$($[(CH_3)_4N]_3[\alpha\text{-}PW_{11}O_{39}\{cis\text{-}Pt^{II}(NH_3)_2\}_2] \cdot 10H_2O$), TMA-Si-2Pt—$NH_3$($[(CH_3)_4N]_4[\alpha\text{-}SiW_{11}O_{39}\{Cis\text{-}Pt^{II}(NH_3)_2\}_2] \cdot 13H_2O$), and TMA-Ge-2Pt—$NH_3$($[(CH_3)_4N]_4[\alpha\text{-}GeW_{11}O_{39}\{cis\text{-}Pt^{II}(NH_3)_2\}_2] \cdot 11H_2O$) synthesized in the same method were evaluated in the following procedures. The photocatalytic activity of TMA-P-1Pt-ppz was evaluated in the same manner and compared with the photocatalytic activity of the binuclear component.

Each polyoxometalate compound in an amount containing 2.0 μmol of platinum atoms, 2.5 μmol of eosin Y, 10 mL of water, and 100 mM of triethanolamine (TEA) were mixed to prepare a reaction solution for a photocatalytic reaction in which hydrogen was generated from water. Light of 400 nm or more was emitted to the reaction solution in an environment at 25° C. and the amount of hydrogen generated by the photocatalytic reaction was quantified. The amount of $H_2$ generated by the reaction for 1 hour and the turnover number (TON, 2×(amount of $H_2$ generated (mol)/amount of Pt atoms (mol)) as an index of the photocatalytic activity were measured. The measurement results are shown in Table 2.

TABLE 2

| Catalyst (μmol of Pt) | Amount of H₂ generated (μmol) | TON |
|---|---|---|
| TMA—P—1Pt-ppz (2.0) | 139.0 | 139 |
| TMA—P—2Pt—NH₃ (2.0) | 77.0 | 77 |
| TMA—Si—2Pt—NH₃ (2.0) | 38.3 | 38 |
| TMA—Ge—2Pt—NH₃ (2.0) | 50.4 | 50 |
| TMA—Al—2Pt—NH₃ (2.0) | 41.0 | 41 |
| TMA—B—2Pt—NH₃ (2.0) | 35.0 | 35 |
| Cs—Ge—2Pt-bpy (2.0) | 2.93 | 3 |
| Cs—Ge—2Pt-phen (2.0) | <1 | <1 |

As shown in Table 2, TMA-P-1Pt-ppz which was a mononuclear polyoxometalate compound showed a significantly higher turnover number than various binuclear polyoxometalate compounds.

4-2. Sintered Body of Polyoxometalate Compound

Each of Cs—P-1Pt—NH₃, Cs—P-2Pt—NH₃ and Cs—P-1Pt(NH₃)-1Pd(bpy) was sintered by heating in a crucible to obtain a sintered body of a polyoxometalate compound. Conditions for sintering were as follows.

Cs—P-1Pt—NH₃: 300° C., 5 hours
Cs—P-2Pt—NH₃: 300° C., 5 hours
Cs—P-1Pt(NH₃)-1Pd(bpy): 500° C., 5 hours Hereinafter, respective sintered bodies will be abbreviated as "Cs—P-1Pt-300(5 h)," "Cs—P-2Pt-300(5 h)" and "Cs—P-1Pt(NH₃)-1Pd(bpy)-500(5 h)."

Each polyoxometalate sintered body in an amount containing 0.6 to 3.0 μmol of platinum atoms, 200 mg of TiO₂ particles (anatase:rutile=80:20), and 20 mL of a methanol aqueous solution (methanol:water (volume ratio)=20:80) were mixed to prepare a reaction solution for a photocatalytic reaction in which hydrogen was generated from water. The amount of the polyoxometalate sintered body was adjusted to an amount corresponding to 0.6 μmol of platinum atoms shown in Table 3.

Light of 400 nm or more was emitted to the reaction solution in an environment at 25° C. and the amount of hydrogen generated by the photocatalytic reaction was quantified. The amount of H₂ generated after 6 hours and the turnover number (TON, 2×(amount of H₂ generated (mol)/amount of Pt atoms (mol)) as an index of the photocatalytic activity were measured. For comparison, the photocatalytic activities of the platinum binuclear polyoxometalate compound Cs—P-2Pt—NH₃ before sintering and commercially available platinum black were evaluated in the same manner. The sintered bodies showed a very high turnover number.

TABLE 3

| Catalyst (μmol of Pt) | Amount of H₂ generated (μmol) | TON |
|---|---|---|
| Cs—P—1Pt-300(5 h) (0.6) | 1,106 | 3,688 |
| Cs—P—2Pt-300(5 h) (0.6) | 636 | 2,121 |
| Cs—P—1Pt(NH₃)—1Pd(bpy)-500(5 h) (0.6) | 896 | 3,039 |
| Cs—P—2Pt—NH₃ (0.6) | 524 | 1,747 |
| Platinum black (3.0) | trace | <1 |

Figure 10:
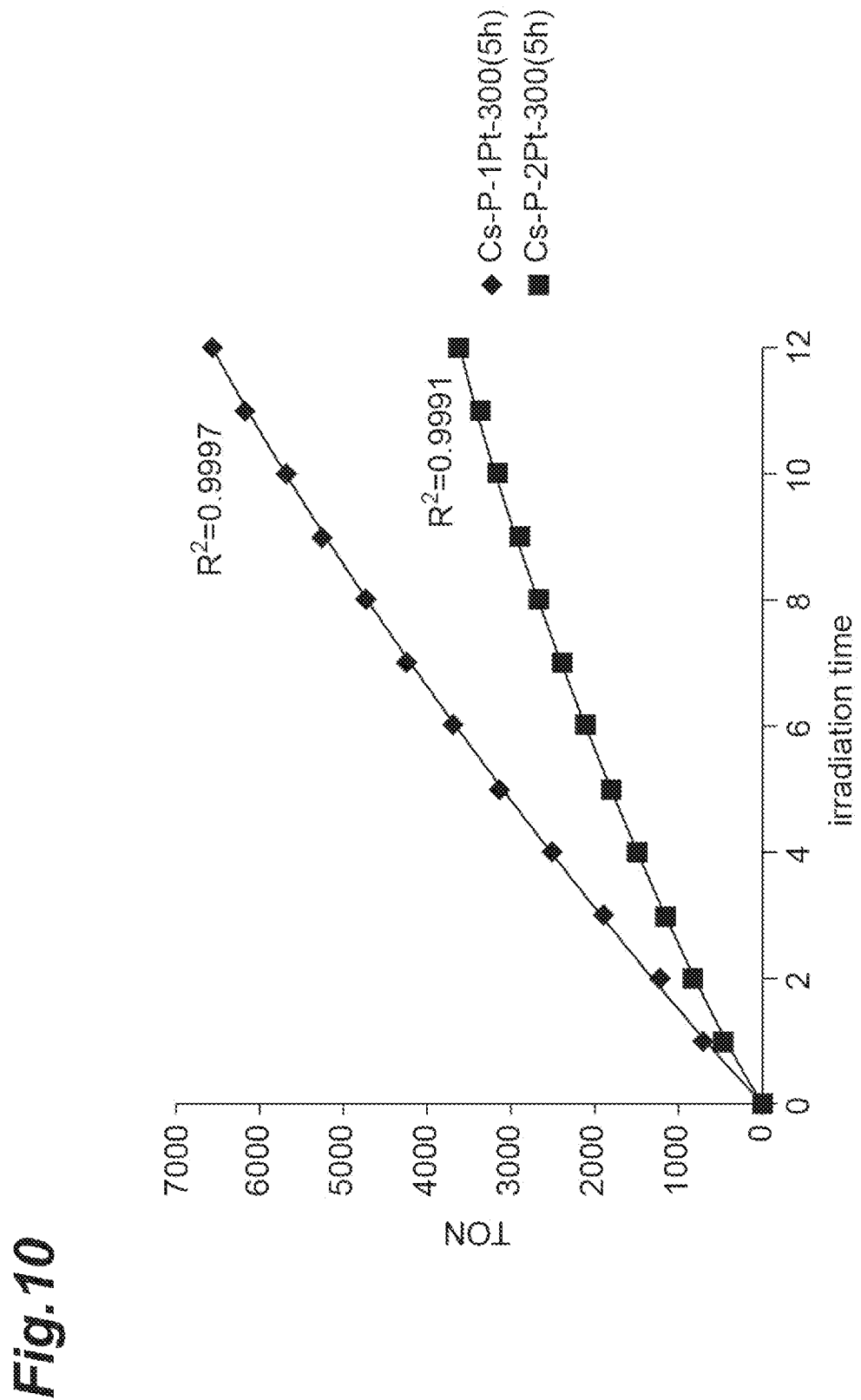
FIG. 10 is a graph showing the relationship between a turnover number for a sintered body of a polyoxometalate compound and a light irradiation time.

Cs—P-1Pt-300(5 h) and Cs—P-2Pt-300(5 h) were subjected to the test until the light irradiation time reached 12 hours. FIG. 10 is a graph showing the relationship between the turnover number TON and the light irradiation time. In the reaction for a long time, it was confirmed that the photocatalytic activity of Cs—P-1Pt-300(5 h) was less likely to decrease than that of Cs—P-2Pt-300(5 h).

REFERENCE SIGNS LIST

3: Polyoxometalate, 3A, 3B: Base unit, 10: Defect site, 21: Metal-substituted polyoxometalate (mononuclear type) 22: Metal-substituted polyoxometalate (binuclear type), M¹ (First) substituting metal atom, M²: Second substituting metal atom, L¹: (First) organic ligand, L²: Second organic ligand.

The invention claimed is:

1. A polyoxometalate compound comprising a metal-substituted polyoxometalate and a counter ion thereof,
   wherein the metal-substituted polyoxometalate comprises:
   a polyoxometalate having one or more defect sites;
   a substituting metal atom introduced into the defect sites; and
   an organic ligand coordinately bonded to the substituting metal atom,
   wherein the substituting metal atom is divalent platinum or palladium,
   wherein the organic ligand is a bidentate ligand comprising an aliphatic heterocycle comprising two nitrogen atoms coordinately bonded to the substituting metal atoms, the organic ligand being selected from a group consisting of L1, L2, L3, and L4,

(L1)

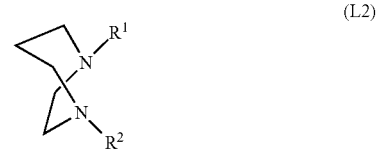

(L2)

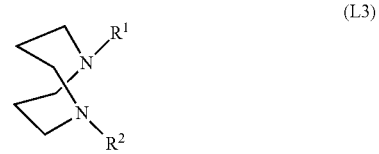

(L3)

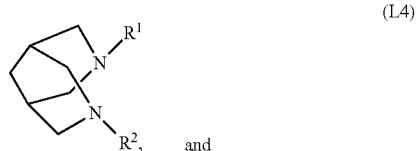

(L4)

and wherein the one substituting metal atom is introduced into each of the one or more defect sites.

2. A method for producing the polyoxometalate compound according to claim 1, comprising:
   in a reaction solution comprising a polyoxometalate having one or more defect sites and a metal complex having a central metal and an organic ligand, reacting the polyoxometalate with the metal complex to generate a metal-substituted polyoxometalate,
   wherein the metal-substituted polyoxometalate comprises:

the polyoxometalate;
a substituting metal atom that is the central metal introduced into the defect sites; and
the organic ligand coordinately bonded to the substituting metal atom,
wherein the central metal and the substituting metal atom are divalent platinum or palladium,
wherein the organic ligand is a bidentate ligand comprising an aliphatic heterocycle comprising two nitrogen atoms coordinately bonded to the one central metal or the one substituting metal atom, the organic ligand being selected from the group consisting of L1, L2, L3, and L4,

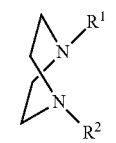
(L1)

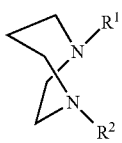
(L2)

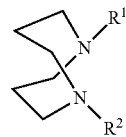
(L3)

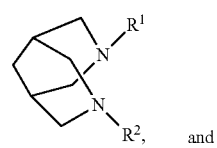
(L4)

and wherein, in the metal-substituted polyoxometalate, the one substituting metal atom is introduced into each of the one or more defect sites.

3. The method according to claim 2,
wherein the organic ligand is N,N'-dimethylpiperazine.

* * * * *